United States Patent [19]

Abdallah et al.

[11] 4,079,130
[45] Mar. 14, 1978

[54] ANTIDEPRESSANT PHENYLAZOIMIDAZOLES

[75] Inventors: Abdulmuniem H. Abdallah; Philip J. Shea, both of Midland, Mich.

[73] Assignee: The Dow Chemical Company, Midland, Mich.

[21] Appl. No.: 794,435

[22] Filed: May 6, 1977

Related U.S. Application Data

[63] Continuation-in-part of Ser. No. 754,798, Dec. 27, 1976, abandoned.

[51] Int. Cl.² ............................................. A61K 31/655
[52] U.S. Cl. ..................................................... 424/226
[58] Field of Search ......................................... 424/226

[56] References Cited

PUBLICATIONS

Chem. Abst., 72 – 11427a (1957).
J. Chem. Soc., 115, 226 (1919).
J. Chem. Soc., 117, 1426 (1920).

*Primary Examiner*—Stanley J. Freidman
*Attorney, Agent, or Firm*—James W. Ambrosius

[57] ABSTRACT

A method for treating Central Nervous System depression and anxiety in a mammal by administering internally to the mammal an effective psychoactive amount of a phenylazoimidazole compound.

11 Claims, No Drawings

ANTIDEPRESSANT PHENYLAZOIMIDAZOLES

CROSS REFERENCE TO RELATED APPLICATION

This is a continuation-in-part of copending application Ser. No. 754,798, filed Dec. 27, 1976, now abandoned.

BACKGROUND OF THE INVENTION

Halo-substituted phenylazoimidazoles are described at CA 72:11427a (Khim. Geterotsikl Soedin 916-22, 1969). Other substituted phenylazoimidazoles are shown in *J. Chem. Soc.*, 115, 226 (1919) and in *J. Chem. Soc.*, 117, 1426 (1920). None of the references cited disclose the use of the compounds to treat an animal.

U.S. Pat. No. 3,489,630 discloses the use of 2-arylhydrazino-imidazoline-(2) as a hypotensive in warm-blooded animals.

SUMMARY OF THE INVENTION

The present invention is directed to a method of treating depression and anxiety in a mammal using a compound of the formula

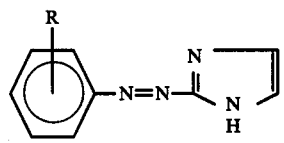

wherein R is located on either the 2-, 3-, or 4-position of the phenyl ring and is selected from the group consisting of hydrogen, halo, nitro, cyano, methyl, and ethyl.

The invention also includes the pharmaceutically-acceptable salts of the phenylazoimidazoles used in the practice of the present invention. As used in the specification and claims, the term "pharmaceutically-acceptable salts" refers to non-toxic acid addition salts of the phenyl-azoimidazole compounds, the anions of which are relatively innocuous to animals at dosages consistent with good antidepressant and antianxiety activity so that the beneficial effects of the free base are not vitiated by the side effects ascribable to the anions. Pharmaceutically-acceptable salts include those derived from mineral acids such as hydrochloric and sulfuric and from organic acids such as lactic, maleic, succinic, fumaric, glutaric, citric, malic, p-toluenesulfonic, methanesulfonic, and tartaric acid and the like.

In general, the compounds of the present invention are administered in daily dosages of from about 0.5 mg to about 100 mg of active ingredient per kilogram of body weight to relieve depression and/or anxiety in a mammal. The compounds are administered internally to a mammal either orally or parenterally by subcutaneous, intravenous or intraperitoneal injection or the like, or by implantation or the like, oral administration being preferred. The effective psychoactive amount of the compounds of the invention to be adminstered internally to a mammal, that is the amount which is effective to substantially relieve a mammal of the symptoms of depression and/or anxiety, can vary depending upon such factors as the animal treated, the particular compound administered, the period of administration, and the method of administration.

DETAILED DESCRIPTION OF THE INVENTION

Compounds used in the practice of the present invention may be prepared by diazotization of substituted aniline in the conventional manner. The diazonium salt is then coupled with imidazole at the 2-position. The general reactions may be summarized as follows:

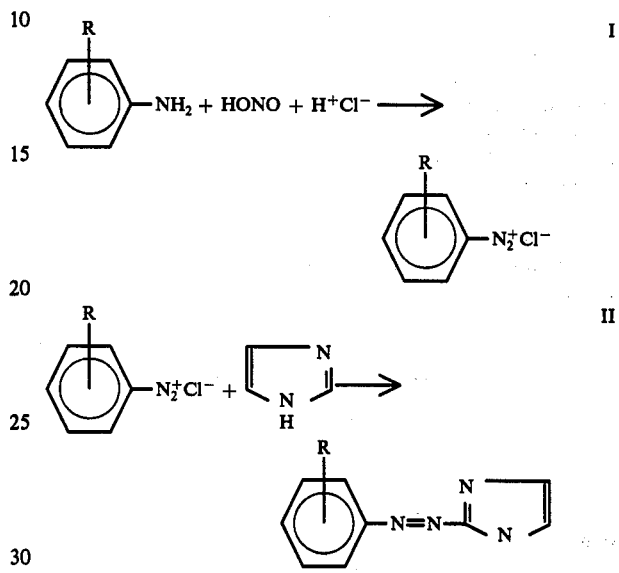

wherein R is the substitution as defined above.

As noted above, compounds used in the method that is the subject of the present invention are effective antidepressant and antianxiety agents when used as described herein. It has been found that compounds having no substitution on the phenyl ring and those substituted in the 2-position with a moiety selected from the group consisting of chloro, fluoro, and cyano were particularly preferred as antidepressant and antianxiety agents when used according to the invention. Other substitutions described in the 2- or 3-position while less active were also found to be operable. Compounds with substitutions in the 4position generally showed poor activity as an antidepressant, but were active as an antianxiety agent.

The following examples and explanation serve to further clarify the present invention but are not to be construed as a limitation thereon.

EXAMPLE 1

Preparation of 2-((2-chlorophenyl)azo)-1H-imidazole

Ice water (750 cc) and concentrated hydrochloric acid (250 cc) were stirred and cooled in an ice bath. Upon the addition of 2-chloroaniline (128.0 grams, 1.0 mole) to the cooled reaction mass, a white solid precipitated out. The resulting mixture was stirred at about 0°C as sodium nitrate (69.0 grams, 1.0 mole) was added in portions over a period of about 15 minutes. After the addition was complete the reaction mass was stirred for an additional 15 minutes after which 68.0 grams (1.0 mole) of imidazole were added. The reaction mass was stirred vigorously as anhydrous sodium carbonate (160.0 grams) was added. The mixture was stirred for 3 hours after which the orange crystals were filtered and washed with water. The damp crystals were mixed with dilute hydrochloric acid and stirred at room temperature for about one hour. The mixture was filtered and the insoluble material discarded. The filtrate was made basic with sodium carbonate. The yellow crystals of 2-((2-chlorophenyl)azo)-1H-imidazole was filtered off and washed with water. The product was recrystallized from ethanol. The proposed structure was confirmed by IR and NMR spectra. The melting point was 195°–196° C.

EXAMPLE 2

The hydrochloride salt of 2-((2-chlorophenyl)-azo)-1H-imidazole was prepared by treating 41.2 grams (0.20 mole) of the product obtained in Example 1 with 40.0 cc of concentrated hydrochloric acid in 600 cc of methanol. The 2-((2-chlorophenyl)azo)-1H-imidazole hydrochloride was found to have a melting point of 212°–215° C.

Using the general methods outlined above, a number of other phenylazoimidazoles having the general formula

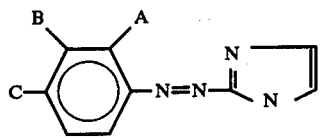

were prepared. These compounds are listed in Table I below.

TABLE I

| Example No. | A= | B= | C= |
|---|---|---|---|
| 3 | F | H | H |
| 4 | H | H | H |
| 5 | $CH_3$ | H | H |
| 6 | Br | H | H |
| 7 | I | H | H |
| 8 | $NO_2$ | H | H |
| 9 | CN | H | H |
| 10 | H | $CH_3$ | H |
| 11 | H | Cl | H |
| 12 | H | H | $CH_3$ |
| 13 | Cl | H | $CH_3$ |
| 14 | H | H | Cl |

In addition to the free bases described above, the hydrochloride salts were prepared for the compounds of Example 3, Example 4 and Example 14.

In practicing the method of the invention, one or more phenylazoimidazoles is administered internally to a mammal by a route effective to introduce an effective psychoactive amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood via the gastrointestinal tract. The phenylazoimidazoles are orally effective, and generally have a higher ratio of toxic dose to effective dose when orally administered, and this route is preferred. The effective amount of phenylazoimidazole compounds to be administered can also be referred to as a "psychoactive amount" (amount sufficient to alleviate Central Nervous System depression and/or anxiety). Likewise, the terms antidepressant amount and antianxiety amount refers to the amount sufficient to alleviate Central Nervous System depression and anxiety, respectively.

The psychoactive amount of compound, that is, the amount of the phenylazoimidazole compound sufficient to provide the desired effect depends on various known factors such as the size, type, age and condition of the animal to be treated, the particular imidazole or pharmacologically-acceptable salt employed, the route and frequency of administration, the type and degree of Central Nervous System condition involved, the time the compound is administered relative to prior and subsequent presentation of food and liquids, etc. In particular cases, the dosage to be administered can be ascertained by conventional range finding techniques, for example, by observing the effect produced at different dosage rates.

Generally, the compound is administered at a daily dosage rate of from about 0.5 to about 100 mg/kg of bodyweight with about 0.5 to about 45 being preferred. Higher dosage rates may be employed, for example, when the compound is administered orally in a timed release dosage form. In the case of mammals suffering from Central Nervous System depression and/or anxiety (exhibiting symptoms of depression and/or anxiety), administration of a psychoactive amount of the phenylazoimidazole compound is preferably repeated at predetermined intervals. It is generally desirable to administer the individual dosages at the lowest psychoactive amount which provides the desired continuity consonant with a convenient dosing schedule.

In practicing the method of the invention, the active ingredient is preferably incorporated in a composition comprising a pharmaceutical carrier and from about 0.001 to about 95 percent by weight of the compound or a pharmacologically-acceptable salt thereof. The term "pharmaceutical carrier" refers to known pharmaceutical excipients useful in formulating pharmacologically-active compounds for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active amidine compound can be formulated in conventional timed release capsule or tablet formulations.

Preferred compositions include sterile injectable solutions containing from about 0.001 to about 10 percent by weight of the active compound in a pharmaceutical carrier suitable for injection, such as isotonic saline solution, Ringer's Injection USP, and lactated Ringer's USP, and the like. Preferred compositions for oral use include unit dosage forms such as capsules and compressed tablets, containing a pharmaceutical carrier and from about 1 to about 150 milligrams of amidine compound per unit.

The following examples further illustrate the method that is the present invention.

EXAMPLE 15

Separate groups of mice and the same origin and past history (5 mice per group) were administered 2-((2- fluorophenyl)azo)-1H-imidazole (Example 3) in an aqueous carrier. Different groups were administered the compound by intraperitoneal injection at various dosage rates. Thirty minutes after the administration of the test compound, the mice were administered reserpine at a dosage rate of 2.5 milligrams per kilogram by intraperitoneal injection. Separate groups of similar mice were similarly administered 2.5 milligrams of reserpine per kilogram 30 minutes after administration of various dosages of the known antidepressant. The mice were then observed for 45 minutes for symptoms of reserpine-induced depression.

In repeated prior check observations, the administration of 2.5 milligrams per kilogram (mg/kg) of reserpine intraperitoneally to mice has been observed to result in a classical progression of symptoms beginning with a characteristic dropping of the eyelids (ptosis) and later culminating in a generalized depression with decreased spontaneous motor activity and decreased responsiveness to auditory and tactile stimuli. Protection from reserpine-induced depression is indicated by the absence of the characteristic ptosis.

The results were employed to calculate the dose effective to protect 50 percent of the mice ($ED_{50}$) by classical, statistical procedures. The imidazole was found to have an $ED_{50}$ of 11 mg/kg. In other operations, the intraperitoneal acute 50 percent lethal dose ($LD_{50}$) was found to be 147 mg/kg, the results corresponding to a therapeutic index $$LD_{50}/ED_{50}$$

of 13.4.

EXAMPLE 16

The procedure of Example 15 was repeated using oral administration of 2-((2-fluorophenyl)azo)-1H-imidazole (Example 3) instead of intraperitoneal injection. The oral $ED_{50}$ was found to be 11 mg/kg.

Using the general procedure outlined above, the $ED_{50}$'s were calculated for some of the other imidazoles herein disclosed. The results are shown in Table II below.

TABLE II

| Compound Example No. | Intraperitoneal $ED_{50}$ (mg/kg) | Oral $ED_{50}$ (mg/kg) | Acute Toxicity $LD_{50}$ (mg/kg) |
| --- | --- | --- | --- |
| 1 | 20 | 23 | greater than 562 |
| 2 | 17 | 32 | 316 |
| 4 | 20 | 24 | 316 |
| 5 | 42 | 43 | — |
| 6 | 23 | 79 | greater than 562 |
| 7 | — | 75 | greater than 562 |
| 9 | 20 | 19 | 147 |
| 10 | 27 | — | 316 |
| 11 | 24 | 32 | 178 |

The data indicate that the compounds shown in Table II while somewhat less active than the compound of Example 3 show significant activity as antidepressant agents. The $ED_{50}$ of the compound 2-((2-nitrophenyl)azo)-1H-imidazole (Example 8) was not determined but the compound was found to be active as an antidepressant. The compounds of Example 12, 13 and 14 were found to be essentially inactive as antidepressant agents under the conditions of the demonstration.

EXAMPLE 17

Antianxiety agents tend to block isolation-induced aggression in mice. Aggression was established in untrained mice by isolating them in individual cages for a period of four weeks. At the end of that period, the mice were paired for three minutes on three test days within one week to establish the absence or presence of aggression. During pairing, one mouse was always in the home cage, and the other was the intruder. If the pair of mice fought at least two of three test sessions, they were used for antianxiety demonstration.

On test days, each dose of test drug was administered by intraperitoneal injection to five pairs of mice; five additional pairs received only the vehicle and served as controls. Each drug was tested at three doses 10.0 mg, 21.5 mg, and 46.4 mg per kilogram of body weight. Thirty minutes after injection, the intruder was placed in the home cage of his opponent, and aggression was recorded as absent or present. When aggression was present, the intruder was removed immediately so that dominance was not established. Using the same procedure as employed in Examples 15 and 16, $ED_{50}$'s were established for each compound. The results are shown in Table III below.

TABLE III

| Compound Example No. | Intraperitoneal $ED_{50}$ (mg/kg) |
| --- | --- |
| 1 | no data |
| 2 | 13.3 |
| 3 | 23.7 |
| 4 | 27.1 |
| 5 | very weak activity |
| 6 | 28.7 |
| 7 | 31.6 |
| 8 | 27.1 |
| 9 | 12.6 |
| 10 | 5.84 |
| 11 | 24.5 |
| 12 | 28.7 |
| 13 | 25.5 |
| 14 | 4.3 |

These data indicate that the compounds disclosed herein when used according to the present method can be used to control anxiety in a mammal. The compounds 2-((3-methylphenyl)azo)-1H-imidazole (Example 10) and 2-((4-chlorophenyl)azo)-1H-imidazole (Example 14) are particularly preferred in controlling anxiety in a mammal using the present method.

What is claimed is:

1. A method for alleviating symptoms of Central Nervous System depression and anxiety in a mammal which comprises administering internally to said mammal a psychoactive amount of a compound having the formula

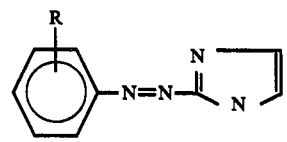

or a pharmaceutically-acceptable salt thereof wherein R is attached at the 2-, 3-, or 4-position and is selected from the group consisting of hydrogen, halo, nitro, cyano, methyl and ethyl.

2. A method for alleviating symptoms of Central Nervous System depression in a mammal which comprises administering internally to said mammal an antidepressant amount of a compound having the formula

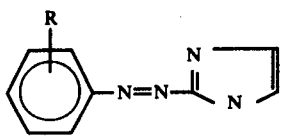

or a pharmaceutically-acceptable salt thereof wherein R is attached at the 2- or 3-position and is selected from the group consisting of hydrogen, halo, nitro, cyano, methyl and ethyl.

3. The method of claim 2 wherein R is selected from the group consisting of hydrogen, chloro, fluoro, and cyano.

4. The method of claim 3 wherein R is attached at the 2-position.

5. The method of claim 4 wherein the compound is 2-((2-chlorophenyl)azo)-1H-imidazole or a pharmaceutically-acceptable salt thereof.

6. The method of claim 4 wherein the compound is 2-(phenylazo)-1H-imidazole or a pharmaceutically-acceptable salt thereof.

7. The method of claim 4 wherein the compound is 2-((2-cyanophenyl)azo)-1H-imidazole or a pharmaceutically-acceptable salt thereof.

8. A method for alleviating symptoms of Central Nervous System anxiety in a mammal which comprises administering internally to said mammal an antianxiety amount of a compound having the formula

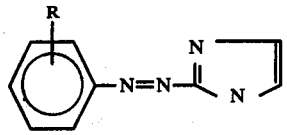

or a pharmaceutically-acceptable salt thereof wherein R is attached at the 2-, 3-, or 4-position and is selected from the group consisting of hydrogen, halo, nitro, cyano, methyl and ethyl.

9. The method of claim 8 wherein the compound is 2-((2-cyanophenyl)azo)-1H-imidazole or a pharmaceutically-acceptable salt thereof.

10. The method of claim 8 wherein the compound is 2-((3-methylphenyl)azo)-1H-imidazole or a pharmaceutically-acceptable salt thereof.

11. The method of claim 8 wherein the compound is 2-((4-chlorophenyl)azo)-1H-imidazole or a pharmaceutically-acceptable salt thereof.

* * * * *

UNITED STATES PATENT AND TRADEMARK OFFICE
CERTIFICATE OF CORRECTION

PATENT NO. : 4,079,130

DATED : March 14, 1978

INVENTOR(S) : Abdulmuniem H. Abdallah and Philip J. Shea

It is certified that error appears in the above-identified patent and that said Letters Patent are hereby corrected as shown below:

Title Page under "References Cited", first line, please change "1957" to -- 1969 --;

Column 1, line 18 "3,489,630" should read -- 3,480,630 --;

Column 2, line 44 "4position" should read -- 4-position --;

Column 1, line 62 "adminstered" should read -- administered --;

Column 4, line 67 "mice and the" should read -- mice of the --.

Signed and Sealed this

Tenth Day of October 1978

[SEAL]

Attest:

RUTH C. MASON
Attesting Officer

DONALD W. BANNER
Commissioner of Patents and Trademarks